(12) United States Patent
West et al.

(10) Patent No.: US 12,226,621 B1
(45) Date of Patent: Feb. 18, 2025

(54) DRUG SUPPLY CARTRIDGE WITH VISUAL USE INDICATOR AND DELIVERY DEVICES THAT USE THE SAME

(71) Applicant: Fresenius Kabi Deutschland GMBH, Bad Homburg (DE)

(72) Inventors: Sharon D. West, Elkins Park, PA (US); Jason Zerweck, Media, PA (US)

(73) Assignee: Fresenius Kabi Deutschland GmbH, Bad Homburg (DE)

( * ) Notice: Subject to any disclaimer, the term of this patent is extended or adjusted under 35 U.S.C. 154(b) by 202 days.

(21) Appl. No.: 17/743,092

(22) Filed: May 12, 2022

Related U.S. Application Data (63) Continuation of application No. 17/180,647, filed on Feb. 19, 2021, now Pat. No. 11,344,682.

(51) Int. Cl.
| | |
|---|---|
| *A61M 5/50* | (2006.01) |
| *A61M 5/19* | (2006.01) |
| *A61M 5/28* | (2006.01) |
| *A61M 5/315* | (2006.01) |

(52) U.S. Cl.
CPC ............ *A61M 5/5086* (2013.01); *A61M 5/19* (2013.01); *A61M 5/286* (2013.01); *A61M 5/31511* (2013.01); *A61M 2205/583* (2013.01)

(58) Field of Classification Search
CPC ............ A61M 5/5086; A61M 5/31511; A61M 5/286; A61M 5/19; A61M 2205/583
See application file for complete search history.

(56) References Cited

U.S. PATENT DOCUMENTS

| | | |
|---|---|---|
| 2003/0167036 A1 | 9/2003 | Flaherty |
| 2012/0010594 A1 | 1/2012 | Holt et al. |
| 2015/0374919 A1 | 12/2015 | Gibson |
| 2016/0038689 A1 | 2/2016 | Lee et al. |
| 2016/0199574 A1 | 7/2016 | Ring et al. |
| 2016/0296704 A1 | 10/2016 | Gibson |
| 2016/0354555 A1 | 12/2016 | Gibson et al. |
| 2017/0119969 A1 | 5/2017 | McCullough et al. |
| 2017/0124284 A1 | 5/2017 | McCullough et al. |
| 2017/0147787 A1 | 5/2017 | Albrecht et al. |
| 2017/0182253 A1 | 6/2017 | Folk et al. |
| 2017/0340837 A1 | 11/2017 | Nazzaro et al. |
| 2017/0361015 A1 | 12/2017 | McCullough |
| 2017/0368260 A1 | 12/2017 | McCullough et al. |
| 2018/0021508 A1 | 1/2018 | Destefano et al. |
| 2018/0028747 A1 | 2/2018 | Hanson et al. |
| 2018/0036476 A1 | 2/2018 | McCullough et al. |
| 2018/0085517 A1 | 3/2018 | Laurence et al. |
| 2018/0256823 A1 | 9/2018 | Nazzaro et al. |
| 2018/0272059 A1 | 9/2018 | Marbet et al. |
| 2018/0304014 A1 | 10/2018 | Knudsen et al. |
| 2019/0022306 A1 | 1/2019 | Gibson et al. |
| 2019/0050375 A1 | 2/2019 | Fitzgibbon et al. |
| 2019/0060562 A1 | 2/2019 | Olivas et al. |
| 2019/0083702 A1 | 3/2019 | Nekouzadeh et al. |

(Continued)

FOREIGN PATENT DOCUMENTS

| | | |
|---|---|---|
| WO | 2018081234 A1 | 5/2018 |
| WO | 2018183039 A1 | 10/2018 |

(Continued)

*Primary Examiner* — Bradley J Osinski
(74) *Attorney, Agent, or Firm* — Cook Alex Ltd.

(57) ABSTRACT

A drug delivery device and cartridge wherein the cartridge includes a movable use indicator that indicates whether the cartridge has been opened and/or used.

20 Claims, 9 Drawing Sheets

(56) References Cited

U.S. PATENT DOCUMENTS

| | | |
|---|---|---|
| 2019/0134296 A1 | 5/2019 | Barbedette et al. |
| 2019/0143043 A1 | 5/2019 | Coles et al. |
| 2019/0143047 A1 | 5/2019 | Jazayeri et al. |
| 2019/0151544 A1 | 5/2019 | Stonecipher |
| 2019/0167908 A1 | 6/2019 | Fitzgibbon et al. |
| 2019/0192766 A1 | 6/2019 | Stonecipher |
| 2019/0247579 A1 | 8/2019 | Damestani |
| 2019/0275241 A1 | 9/2019 | Ring et al. |
| 2019/0328965 A1 | 10/2019 | Moberg |
| 2019/0365986 A1 | 12/2019 | Coiner et al. |
| 2019/0374707 A1 | 12/2019 | Damestani et al. |
| 2019/0381238 A1 | 12/2019 | Stonecipher et al. |
| 2020/0023122 A1 | 1/2020 | McCullough et al. |
| 2020/0164145 A1 | 5/2020 | Chang et al. |
| 2020/0164155 A1 | 5/2020 | Mojarrad et al. |
| 2020/0179609 A1 | 6/2020 | Tan-Malecki et al. |
| 2020/0197628 A1 | 6/2020 | McCullough et al. |
| 2020/0206429 A1 | 7/2020 | Hering et al. |
| 2020/0230313 A1 | 7/2020 | Mojarrad et al. |
| 2020/0238004 A1 | 7/2020 | McCullough |
| 2020/0254172 A1 | 8/2020 | Forster et al. |
| 2020/0261648 A1 | 8/2020 | Groszmann et al. |
| 2020/0261657 A1 | 8/2020 | Gibson et al. |
| 2020/0289745 A1 | 9/2020 | Harris et al. |
| 2020/0297927 A1 | 9/2020 | Conrath et al. |
| 2020/0322793 A1 | 10/2020 | Yang |
| 2020/0338271 A1 | 10/2020 | Harris et al. |

FOREIGN PATENT DOCUMENTS

| | | |
|---|---|---|
| WO | 2018226565 A1 | 12/2018 |
| WO | 2019018169 A1 | 1/2019 |
| WO | 2019022950 A1 | 1/2019 |
| WO | 2019022951 A1 | 1/2019 |
| WO | 2019032101 A1 | 2/2019 |
| WO | 2019143753 A1 | 7/2019 |

DRUG SUPPLY CARTRIDGE WITH VISUAL USE INDICATOR AND DELIVERY DEVICES THAT USE THE SAME

RELATED APPLICATIONS

This application is continuation of prior application Ser. No. 17/180,647, filed Feb. 19, 2021, which is hereby incorporated herein by reference.

BACKGROUND

Field of the Disclosure

The present disclosure relates to drug delivery devices. More particularly, the present disclosure relates to devices adhered to the patient's body for automatically delivering a drug to the patient. Even more particularly, the present disclosure relates to drug supply/refill cartridges for resupplying the delivery device, wherein the cartridges have a visual use indicator.

Description of Related Art

Delivery of liquid drugs to a patient via injection using a needle or syringe is well-known. More recently, devices that automate the delivery of liquid drugs have been introduced. These devices (which are commonly referred to as "on-body devices" or "on-body injectors") are mounted or otherwise secured to the body of the patient (e.g., to the arm or abdomen) and remain in place for an extended amount of time (on the order of hours or days), injecting an amount of the drug into the body of the patient at one or more scheduled times. For example, a device may be configured to deliver a drug over the span of 45 minutes, with delivery beginning 27 hours after the device has been activated and applied to a patient (to ensure that the drug is not delivered sooner than 24 hours after a medical procedure or treatment). These devices improve upon manual methods by obviating the need for the patient to inject themselves with the drug (which carries heightened risks of the patient improperly administering the injection or injecting the drug at an inappropriate time) or to return to a medical facility for one or more injections by a technician or medical professional.

Figure 1:
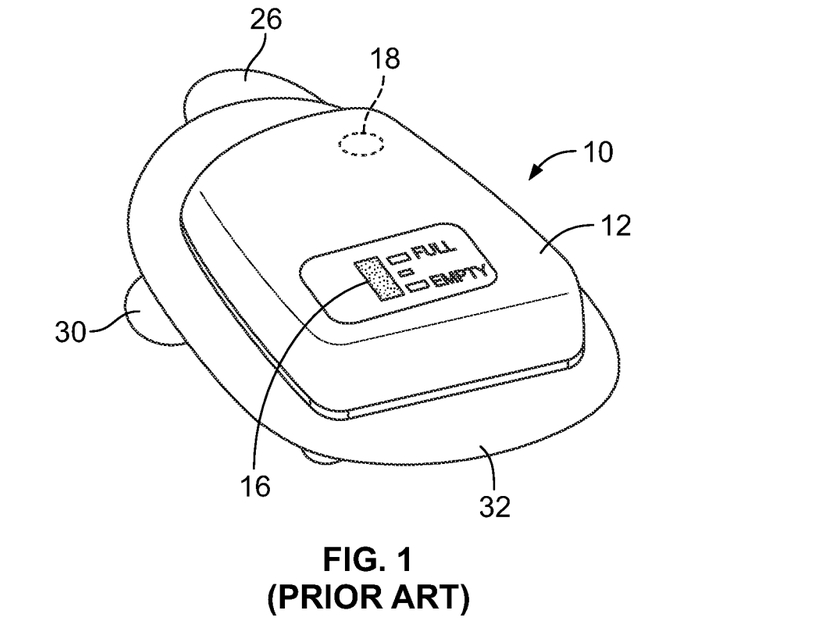
FIG. 1 is a top perspective view of a drug delivery device according to conventional design.
Figure 2:
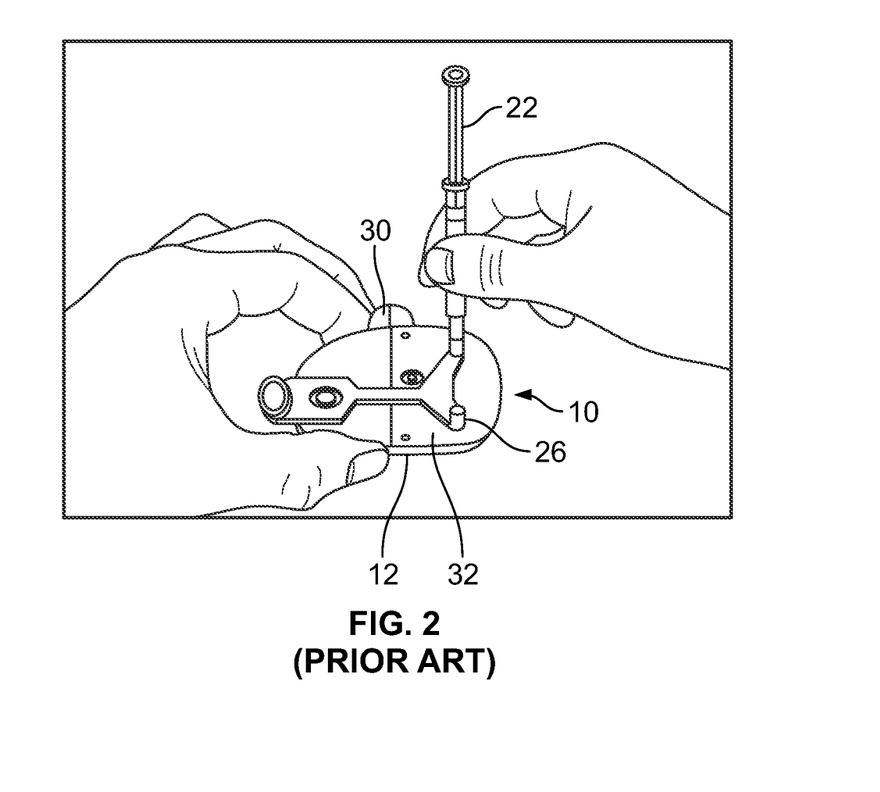
FIG. 2 is a bottom perspective view of the drug delivery device of FIG. 1.
Figure 3:
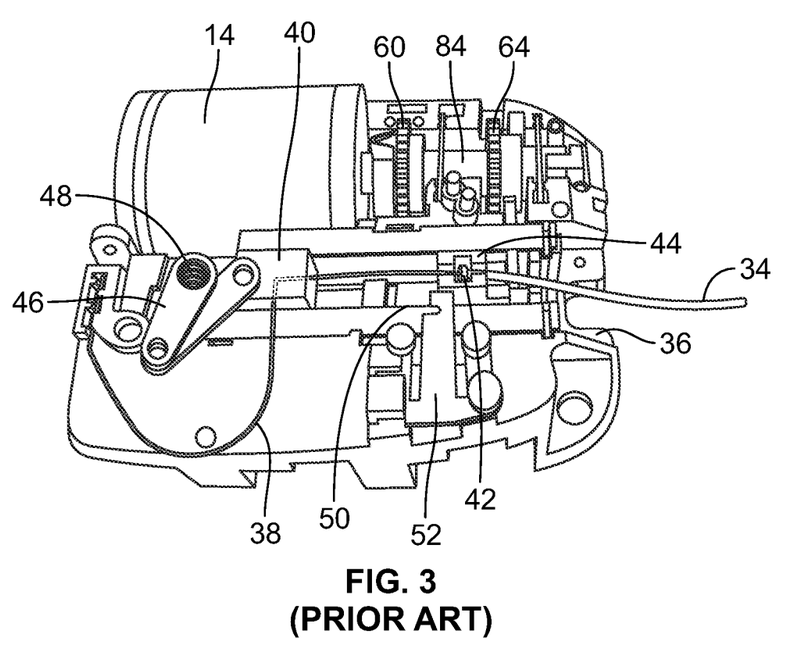
FIG. 3 is a top perspective view of the interior components of the drug delivery device of FIG. 1.
Figure 4:
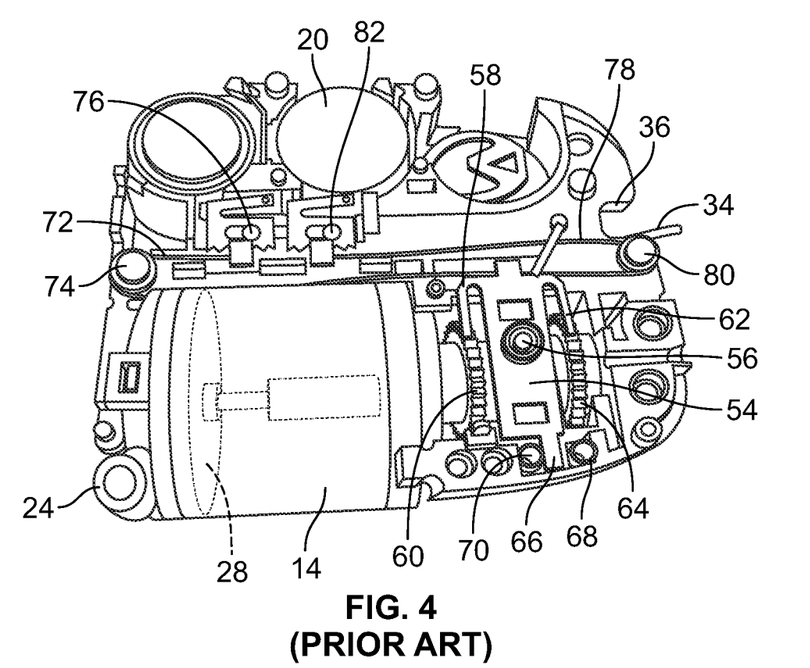
FIG. 4 is a bottom perspective view of the interior components of the drug delivery device of FIG. 1.

One known on-body device 10 is shown in FIGS. 1 and 2. The device 10 of FIG. 1 includes a housing 12 that contains or encloses the functional components of the device 10, which are shown in FIGS. 3 and 4.

The internal components of the device 10 include a reservoir 14 that is configured to be filled with a liquid drug to be delivered to the patient. An upper surface of the housing 12 includes a fill indicator 16 that provides a visual indication of the amount of fluid in the reservoir 14. In addition to the fill indicator 16, the upper surface of the housing 12 may include printed information, such as information regarding the drug to be delivered. The upper surface of the housing 12 may be formed of a translucent material, which allows light from a status light 18 (which may be configured as a light-emitting diode) mounted within the housing 12 (FIG. 1) to be seen through the upper surface of the housing 12. The status light 18 is electrically coupled to a controller or processor (which may be a CPU or MPU configured as a computer chip mounted to a printed circuit board positioned within the housing 12, for example) that carries software for executing a drug delivery routine. The status light 18 receives signals from the controller and emits light to provide information regarding a status of the device 10. This may include emitting differently colored light and/or emitting light in different flashing patterns to indicate different conditions, such as a blinking orange light to indicate that the device 10 is ready to be applied to a patient, a blinking green light to indicate proper operation of the device 10, and a blinking red light to indicate an error or other condition. One or more batteries 20 provides power to the status light 18 and the other electrical components of the device 10.

The drug is injected into the reservoir 14 using a (typically pre-filled) syringe 22 via a port 24 incorporated into the bottom or underside of the housing 12 (FIG. 4) and fluidly connected to the reservoir 14. FIGS. 1 and 2 illustrate an applicator 26 that is removably associated with the underside of the housing 12 and used in combination with the syringe 22 to fill the reservoir 14 via the port 24. The drug is most typically injected into the reservoir 14 by a medical professional immediately before the device 10 is secured to the patient to ensure that the proper drug is supplied, along with the proper amount.

A piston or plunger 28 (FIG. 4) positioned within the reservoir 14 is moved (from left to right, in the orientation of FIG. 4) as the space within the reservoir 14 is filled by the inflowing drug. Movement of the piston 28 into its final position (when the reservoir 14 has been filled with the appropriate amount of the drug) causes a portion of a rod associated with the piston 28 to extend from the reservoir 14 to create an electrical connection, which activates the device 10. Activation of the device 10 may include a signal, such as a buzzer providing an audible indication that the device 10 has been activated and/or a light emitted by the status light 18.

When the device 10 has been activated, it is mounted or secured to the body of the patient. The applicator 26 is first removed from the underside of the housing 12 and discarded, followed by a pull tab 30 being manipulated to remove a release film from an adhesive pad 32 associated with the underside of the housing 12. The housing 12 is then pressed against the body of the patient, with the adhesive pad 32 facing the body. An adhesive present on the adhesive pad 32 causes the adhesive pad 32 (and, hence, the housing 12) to adhere to the body.

Some predetermined time after the device 10 has been activated (which may be on the order of three to five minutes, for example), a distal end portion of a cannula 34 is introduced into the skin of the patient via a cannula window 36 defined in the housing 12 (FIGS. 3 and 4). The cannula 34 (which remains partially positioned within the skin of the patient for as long as the device 10 is in use) is formed of a flexible or semi-rigid material, such as a plastic material, for improved patient comfort.

As the cannula 34 is not itself configured to pierce the skin, an associated needle 38 is provided within the lumen of the cannula 34, with a sharp or beveled distal end of the needle 38 extending out of a distal end of the cannula 34. A midsection of the needle 38 is mounted within a needle carriage 40, while a proximal end 42 of the cannula 34 is mounted within a cannula carriage 44 that is initially positioned directly adjacent to the needle carriage 40. The needle carriage 40 is pivotally connected to an end of a linkage or crank arm 46, with an opposite end of the linkage 46 being associated with a torsion spring 48. At the designated time (e.g., 3-5 minutes after the device 10 has been activated), the controller causes a lever (not visible) to be released, which allows the spring 48 to recoil, in turn rotating the linkage 46, which rotation causes the needle carriage 40 to move along a linear track 50 from a first position adjacent to the spring 48 (FIG. 3) to a second position spaced away from the spring 48. Movement of the needle carriage 40 causes corresponding movement of the cannula carriage 44 along the track 50, with the cannula 34 and the distal portion of the needle 38 moving together in a direction away from the spring 48. Moving the carriages 40 and 44 into the second position causes the sharp distal end of the needle 38 to advance out of the housing 12 via the cannula window 36 and pierce the skin. The cannula 34 is carried by or moves along with the distal portion of the needle 38, such that the needle 38 piercing the skin will also cause the distal end of the cannula 34 to enter into the skin.

Continued recoiling of the spring 48 causes further rotation of the linkage 46, which has the effect of moving the needle carriage 40 back toward the spring 48 (i.e., back toward its first position). Rather than moving along with the needle carriage 40, the cannula carriage 44 is held in its second position (FIG. 3) by a lock or latch 52. As the movement of the needle carriage 40 is not restricted by the lock or latch 52, the needle carriage 40 will return to its first position, while the cannula carriage 44 remains in its second position (with the final positions of both carriages 40 and 44 shown in FIG. 3).

Movement of the needle carriage 40 in a proximal direction away from the cannula carriage 44 causes the needle 38 to partially (but not fully) retract from the cannula 34. In the final condition shown in FIG. 3, the distal end of the needle 38 is positioned within the cannula 34 (e.g., adjacent to a midsection or midpoint of the cannula 34), while the distal end of the cannula 34 remains positioned within the skin. A proximal end of the needle 38 extends into fluid communication with the reservoir 14, such that the needle 38 provides a fluid path from the reservoir 14 to the cannula 34 when the carriages 40 and 44 are in the final condition illustrated in FIG. 3. Due to the distal end of the cannula 34 remaining positioned within the skin, subsequent advancement of the drug out of the reservoir 14 (e.g., 27 hours after the device 10 has been activated) will cause the drug to move into the needle 38 (via the proximal end of the needle 38), through the needle 38 (to its distal end), and into the cannula 34. The drug is then delivered to the patient (e.g., over the course of a 45-minute session) via the distal end of the cannula 34 positioned within the skin.

As for the mechanism by which the drug is advanced out of the reservoir 14, the device 10 includes a lever 54 mounted to a pivot point 56 (FIG. 4). The lever 54 includes a first arm 58 configured and oriented to interact with a first gear 60 and a second arm 62 configured and oriented to interact with a second gear 64. A tab 66 extends from an opposite end of the lever 54 and is configured and oriented to alternately move into and out of contact with two electrical contacts 68 and 70 (electrically coupled to a printed circuit board, which is not shown) as the lever 54 pivots about the pivot point 56.

A first wire or filament 72 extends from the lever 54, around a first pulley 74, and into association with a first electrical contact 76. A second wire or filament 78 extends from the lever 54 in the opposite direction of the first wire 72, around a second pulley 80, and into association with a second electrical contact 82. The wires 72 and 78 (which are commonly referred to as "muscle wires") are formed of a shape memory alloy (e.g., Nitinol), which causes them to heat up and contract when a current flows through them, while being allowed to stretch when the current is removed and the wire 72, 78 cools. Current is alternately applied to the two wires 72 and 78, causing the one carrying a current to heat up and contract while the other one is allowed to stretch. The wire 72, 78 that contacts will pull on the lever 54, causing it to pivot about the pivot point 56. Thus, alternately applying current to the two wires 72 and 78 will cause the wires 72 and 78 to alternately contact and stretch, which in turn causes the lever 54 to pivot back and forth about the pivot point 56.

At the designated time (e.g., 27 hours after the device 10 has been activated), the controller provides commands that cause current to be alternately applied to the muscle wires 72 and 78, which causes the lever 54 to alternately pivot about the pivot point 56 in opposite first and second directions. Pivotal movement of the lever 54 in the first direction will cause the first arm 58 of the lever 54 to engage and rotate the first gear 60 an incremental amount, while pivotal movement of the lever 54 in the second direction will cause the second arm 62 of the lever 54 to engage and rotate the second gear 64 an incremental amount (in the same direction in which the first gear 60 is rotated by the first arm 58). Both gears 60 and 64 are associated with a common shaft 84 (which is shown in FIG. 3 and may be formed with the gears 60 and 64 as a single, molded piece), such that rotation of either gear 60, 64 will cause the shaft 84 to rotate about its central axis. The shaft 84 is mechanically coupled to the piston 28 within the reservoir 14, with rotation of the shaft 84 causing the piston 28 to move toward its initial position (e.g., by a threaded connection whereby rotation of the shaft 84 is translated into movement of the piston 28 along the length of the reservoir 14). As the piston 28 moves toward its initial position (from right to left in the orientation of FIG. 4), it will force the drug out of the reservoir 14 via the proximal end of the needle 38. As described above, the drug will flow through the needle 38, into and through the cannula 34, and into the body of the patient.

After the drug has been delivered (e.g., over the course of a 45-minute session), the controller alerts the patient via a visual cue from the status light 18 and/or an audible cue from the buzzer that drug delivery is complete. Subsequently, the patient removes the device 10 from their skin and discards the device 10.

While devices of the type described above have proven adequate, there is room for improvement of them. For example, there remains a need for an infuser that allows for refilling of the infuser without removing it from the patient.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, a cartridge containing a liquid drug includes a first chamber containing the liquid drug and a second chamber having a gas pressure. The second chamber is configured so that the gas pressure changes from a first pressure to a second pressure, wherein the first pressure is less than the second pressure. Further, the gas pressure in the second chamber has the first pressure when the cartridge is in an unopened and/or unused state, and the gas pressure in the second chamber has the second pressure when the cartridge is in an opened and/or used state. The cartridge also includes a movable visual indicator associated the second chamber. The movable visual indicator is in a first position when the gas pressure of the second chamber has the first pressure and moves to a second position when the gas pressure of the second chamber has the second pressure. The first position of the movable visual indicator indicates that the cartridge is in an unopened and/or unused state, and the second position of the movable visual indicator indicates that the cartridge is in an opened or used state.

In another aspect, a drug delivery device includes a housing containing a drug delivery mechanism. The drug delivery device also includes a replaceable cartridge containing a liquid drug. The replaceable cartridge includes a first chamber containing the liquid drug and a second chamber having a gas pressure. The second chamber is configured so that the gas pressure changes from a first pressure to a second pressure, wherein the first pressure is less than the second pressure. Further, the gas pressure in the second chamber has the first pressure when the cartridge is in an unopened and/or unused state, and the gas pressure in the second chamber has the second pressure when the cartridge is in an opened and/or used state. The cartridge also includes a movable visual indicator associated the second chamber. The movable visual indicator is in a first position when the gas pressure of the second chamber has the first pressure and moves to a second position when the gas pressure of the second chamber has the second pressure. The first position of the movable visual indicator indicates that the cartridge is in an unopened and/or unused state, and the second position of the movable visual indicator indicates that the cartridge is in an opened or used state.

These and other aspects of the present subject matter are set forth in the following detailed description of the accompanying drawings.

DESCRIPTION OF THE ILLUSTRATED EMBODIMENTS

The embodiments disclosed herein are for the purpose of providing a description of the present subject matter, and it is understood that the subject matter may be embodied in various other forms and combinations not shown in detail. Therefore, specific designs and features disclosed herein are not to be interpreted as limiting the subject matter as defined in the accompanying claims.

Figure 5A:
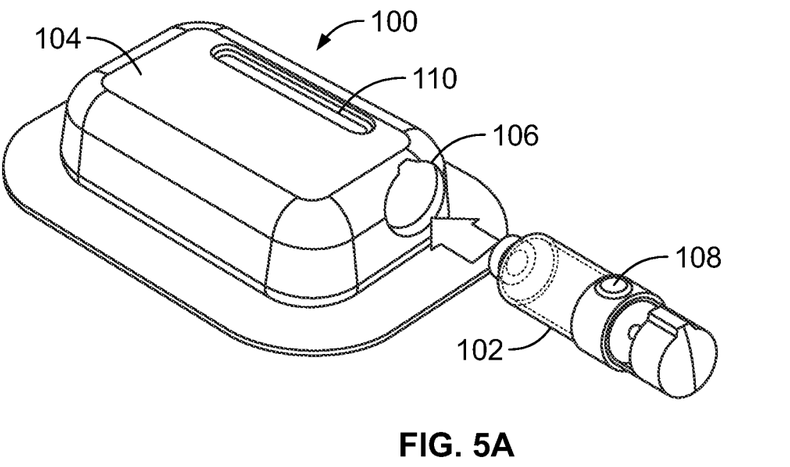
FIG. 5A is a top perspective view of an exemplary drug delivery device of the present disclosure, shown prior to receiving a drug supply cartridge and with a visual use indicator indicating that the cartridge is in an unopened and/or unused state.
Figure 5B:
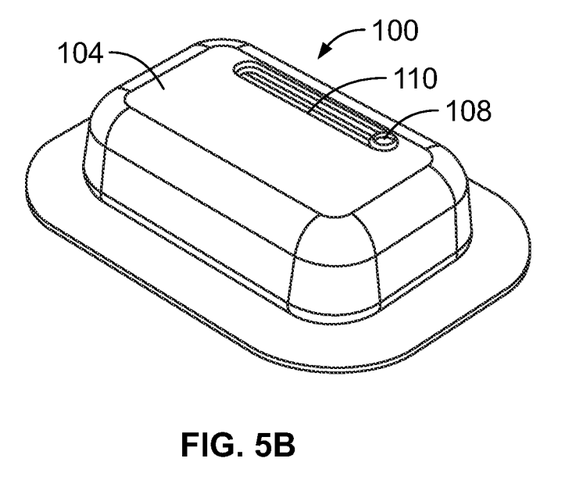
FIG. 5B is a top perspective view of the drug delivery device of FIG. 5A, shown with the drug supply cartridge inserted into the drug delivery device.
Figure 5C:
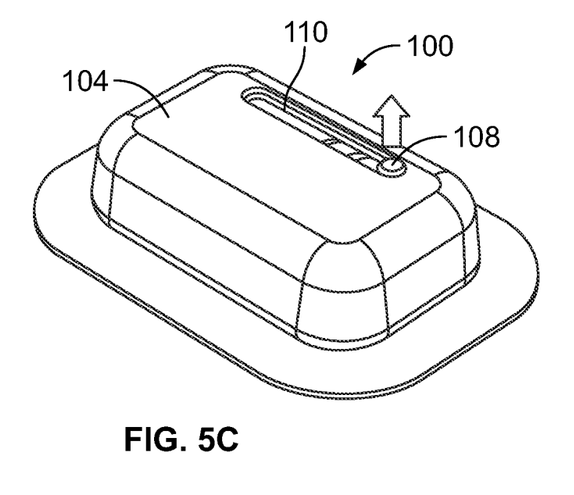
FIG. 5C is a top perspective view of the drug delivery device of FIG. 5B, shown after the drug supply cartridge is fully docked in the drug delivery device and with the visual use indicator indicating that the cartridge is in an opened and/or used state.

FIGS. 5A-5C illustrate an exemplary embodiment of a drug delivery device 100 of the present disclosure. The drug delivery device 100 employs a replaceable or refillable cartridge system for supplying and refilling the delivery device 100 with the drug to be delivered. The methods and devices described herein may be used to deliver any suitable fluid medication to a subject. In an exemplary embodiment, the methods and devices described herein are used to deliver pegfilgrastim to a subject, though other exemplary medications include (without limitation) one or more of the following: adalimumab, rituximab, risankizumab, etanercept, trastuzumab, ado-trastuzumab emtansine, trastuzumab deruxtecan, bevacizumab, infliximab, pegfilgrastim, filgrastim, tocilizumab, golimumab, interferon beta-1a, ranibizumab, denosumab, pembrolizumab, nivolumab, aflibercept, eculizumab, ocrelizumab, pertuzumab, secukinumab, omalizumab, ustekinumab, vedolizumab, daratumumab, dupilumab, atezolizumab, natalizumab, bortezomib, ipilimumab, durvalumab, emicizumab, palivizumab, guselkumab, mepolizumab, panitumumab, ramucirumab, belimumab, abatacept, certolizumab pegol, ixekizumab, romiplostim, benralizumab, evolocumab, canakinumab, obinutuzumab, cetuximab, erenumab, blinatumomab, romosozumab, mirikizumab, inotuzumab, sacituzumab govitecan, enfortumab vedotin, brentuximab vedotin.

During use, a drug supply cartridge 102, containing a supply of a fluid drug or medicant, is docked to the drug delivery device 100 to supply the drug to the delivery device. The drug may be, for example, a liquid drug that is pumped by the delivery device into the patient. After the cartridge 102 is empty or spent, the spent cartridge is removed and a new cartridge is docked to the drug delivery device 100. Thus, the delivery device may include a plurality of refill cartridges 102. In the illustrated embodiment, the delivery device 100 includes a housing 104, which may be attached to a patient's body. The housing 104 include an opening 106 for receiving the cartridge 102 and docking it to the delivery device 100. The housing 104 also may contain any suitable delivery mechanism for delivering the drug to the patient, such as the above-described delivery system.

The cartridge 102 includes a visual use indicator 108 that indicates whether the cartridge 102 is in an unopened and/or unused state or in an opened and/or used state. The visual indicator 108 has a first visual appearance prior to opening and/or use of the cartridge, and a second visual appearance after the cartridge has been opened and/or used. The difference between the first visual appearance and the second visual appearance may be any visual difference sufficient to indicate the state of the cartridge 102 to the user. For example, the first visual appearance, indicating the cartridge 102 is unopened and/or unused, may be a first color, absence of color or a graphical appearance, and the second visual appearance may be a different color, including a color or a different graphical appearance. The visual use indicator may reduce the risk of the user installing or using a previously used or unintentionally opened cartridge. Thus, the visual use indicator may reduce the risk of using a cartridge that has lost its sterility.

As shown in FIGS. 5A and 5B, the visual use indicator 108 has a first appearance that indicates that the cartridge has not been previously used and/or is unopened. This first appearance indicates that the cartridge has not lost its sterility and/or contains a full supply of the drug. Turning to FIG. 5C, when the cartridge 102 is docked to the device 100, the cartridge is placed in fluid communication with the device 100 by, for example, a needle, luer, or any other suitable connection. When the cartridge 102 is opened by the device 100 and/or use of the cartridge 102 has commenced, the visual indicator 108 changes to a second appearance that indicates that the cartridge 102 has been used and/or opened. In the illustrated embodiment, the housing 104 includes a window 110 so that the visual indicator 108 of the cartridge 102 is visible to the user. The window 110 may be a hole in the housing or a transparent portion of the housing 104.

One embodiment of cartridge 102 is shown in FIGS. 6-9. Cartridge 102 includes a body 112 having a shape and size suitable for docking with the delivery device 100 (FIG. 5A). The cartridge 102 includes a port 114 (FIGS. 6 and 8) that fluidically connects with the delivery device 100 to supply the device with the drug to be injected. The cartridge 102 also includes a first chamber or barrel 116 that contains a drug or medicant. The first chamber 116 is in fluid communication with the port 114. A plunger 118 may be located in the first chamber 116. In the illustrated embodiment, the plunger 118 includes a head or stopper 120 and a rod 122. The plunger 118 is operatively connected to and controlled by the delivery device 100. The delivery device 100 moves the plunger 118 within the chamber 116 to push the drug out of the port 114 and into the delivery device 100.

Figure 6:
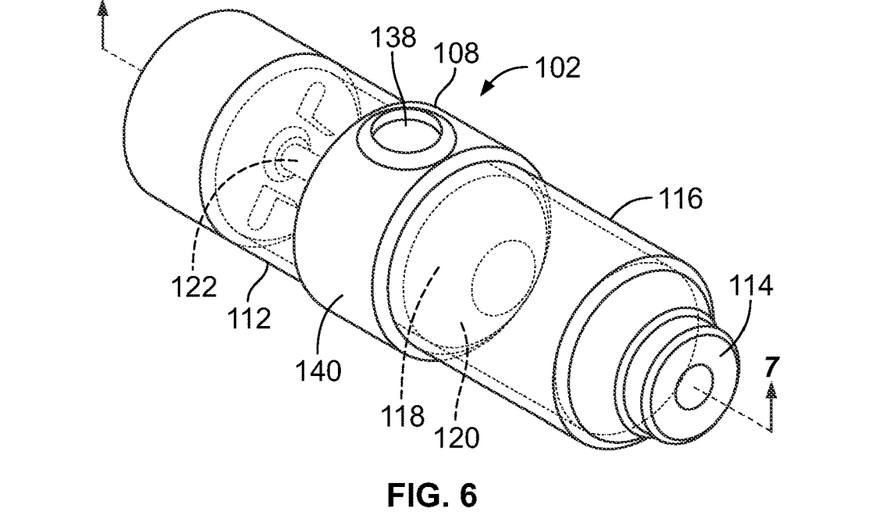
FIG. 6 is a top perspective view of one embodiment of a drug supply cartridge in accordance with the present disclosure, wherein a visual use indicator is in a position that indicates that the cartridge is in an unopened and/or unused state.
Figure 7:
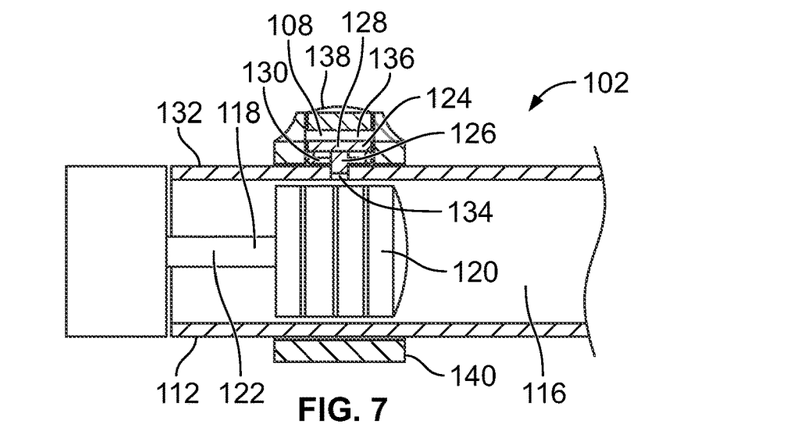
FIG. 7 is a cross-sectional view of the cartridge shown in FIG. 6, taken along line 7-7.
Figure 8:
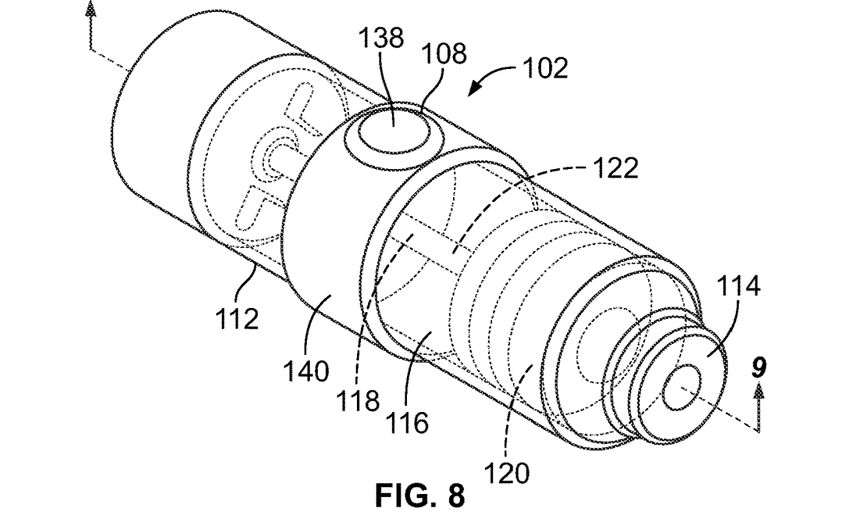
FIG. 8 is a perspective view of the cartridge shown in FIG. 6, wherein the visual use indicator has been moved into a position that indicates that the cartridge is in an opened and/or used state.
Figure 9:
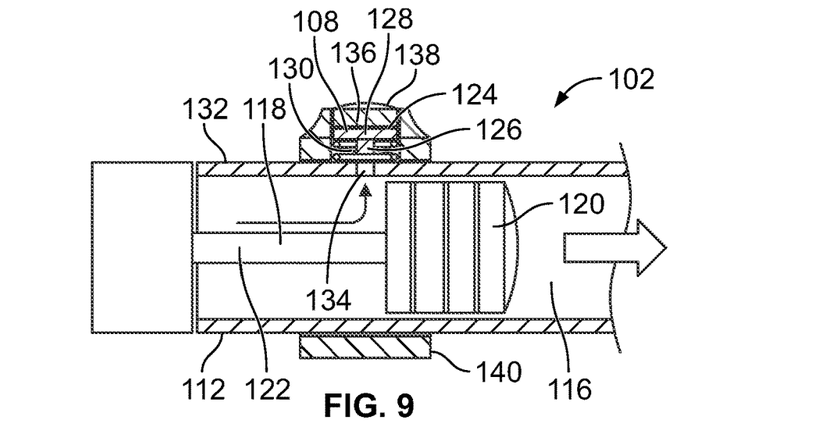
FIG. 9 is cross-sectional view of the cartridge shown in FIG. 8, taken along lines 9-9.

As mentioned above, the cartridge 102 includes a visual use indicator 108 that provides an indication of whether the cartridge 102 is unopened/unused or has been opened/used. FIGS. 6 and 7 illustrate the cartridge 102 in an unopened/unused state and prior to being docked in the delivery device 100 (FIGS. 5A-5C). FIGS. 8 and 9 illustrate the cartridge 102 in the opened or used state. As can be seen by comparing these figures, in FIGS. 6 and 7, the visual indicator 108 is in a first position that provides a visual indication that the cartridge 102 is in the unopened/unused stated. In FIGS. 8 and 9, the visual indicator 108 has moved to the second position that provides a visual indication that the cartridge 102 is in the opened/used state.

Referring to FIGS. 7 and 9, the visual use indicator 108 includes a movable indicator, such as the illustrated button 124. In this embodiment, the button 124 includes a stem 126 and a head 128. The cartridge also includes a biasing member 130, such as a spring, located between head 128 of the button 124 and a wall 132 of the body 112 of the cartridge 102. The biasing member 130 biases the button 124 upward or away from the wall 132 toward the second position, as shown in FIGS. 8 and 9. Referring to FIGS. 7 and 9, cartridge 102 includes a second chamber 134, such as a vacuum chamber, to which the visual use indicator 108 is associated. In this embodiment, the second chamber 134 is defined by a hole in the wall 132 of the body 112 of the cartridge. As used herein the term "vacuum" means a pressure lower than the air pressure of the environment outside of the second chamber 134. In one embodiment the vacuum chamber is lower than atmospheric pressure (about 101325 Pa). The second chamber 134 includes at least one openable seal, sealing the second chamber 134. In the illustrated embodiment, the chamber 134 includes a top seal and a bottom seal. The top seal is defined by the stem 126 of the button 124 of the visual use indicator, wherein the stem covers and/or extends into a top opening of the chamber 134 to seal the opening. The bottom seal is defined by head 120 of the plunger 118, wherein the head 120 covers and seals a bottom opening of the chamber 134. As will be described in greater detail, the second chamber 134 has a gas pressure that changes from a first pressure to a second pressure, wherein the first pressure is less than the second pressure.

Referring to FIG. 7, when the cartridge 102 is in the initial, unused and/or unopened state, the second chamber 134 is sealed and the first pressure of the gas pressure within the chamber 134 is such that the stem 126 defining the top seal of the chamber 134 is held or maintained within the opening of the chamber. In this position, the biasing member 130 (spring) is placed into and held in a compressed state. In this arrangement, the first pressure of the gas pressure within the chamber 134 plus the force of the biasing member 130 (spring force) is less than the force of the external air pressure, and in one embodiment less than atmospheric pressure.

Referring to FIG. 9, when the plunger 118 is advanced, the bottom seal is removed/broken and gas (e.g., air) enters the second chamber 134 through the bottom opening, increasing the gas pressure within the second chamber 134 to a second pressure, which is greater than the first gas pressure. When the gas pressure increases to the second pressure, the stem 126 of the button 124 is released from the opening and the biasing member 130 pushes on the bottom of the head 128 of the button 124, moving it upward and away from the wall 132 of the cartridge 102. In this position, the force of the second pressure of the chamber 134 and the force of the spring is greater than the outer surrounding air pressure.

Optionally, at least a portion of the button 124 may be within a third chamber 136 that includes a window or opening 138. The third chamber 136 may be defined by a support 140, such as the illustrated ring positioned about the body 112 of the cartridge 102. As shown in FIGS. 6 and 7, in the unused and/or unopened state, the head 128 of the button is not visible in the window or opening 138 of the third chamber 136. Referring to FIGS. 8 and 9, in the opened and/or used state, when the pressure in the second chamber 134 changes, the stem 126 of the button 124 is released and the head 128 of the button 124 is moved into a position wherein it is visible to the user, thereby providing a visual indication that the cartridge 102 is opened and/or used.

Figure 7A:
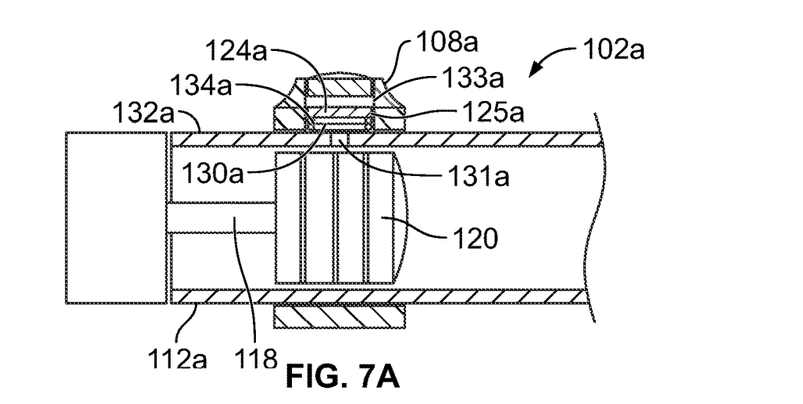
FIG. 7A is a cross-sectional view of the cartridge shown in FIG. 6, taken along line 7-7 and showing an alternative embodiment.
Figure 9A:
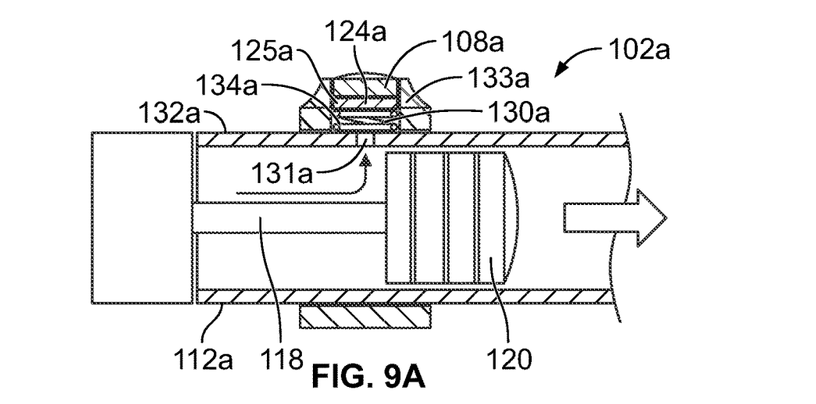
FIG. 9A is cross-sectional view of the cartridge shown in FIG. 8, taken along lines 9-9 and showing another embodiment.

FIGS. 7A and 9A illustrate another embodiment of a visual use indictor 108a, which is similar to that of FIGS. 7 and 9. In this embodiment, the second chamber 134a is defined by a passageway 131a in the wall 132a of the body 112a, sidewall(s) 133a extending outward from wall 132a and the button 124a. The shape of the button 124a and the corresponding sidewall(s) 133a may be any suitable shape, such as disc shaped or polygonal shaped. Additionally, the button 124a does not include a stem as in the previous embodiment, but instead includes a seal(s) 125a located about the periphery of the button 124a. The seal(s) 125a contact the inner surface of the sidewall(s) 133a to seal the chamber 134a. In one embodiment, the seal(s) 125a may be wiper seal(s) that sealing slide along the inner surface of sidewall(s) 133a. In other embodiments, the seal(s) 125a may be any other suitable seal. A biasing member 130a is located in chamber 134a between the wall 132a and the button 124a. The biasing member 130a biases the button 124a upward or away from the wall 132a toward the position, as shown in FIGS. 8 and 9A.

Similar to the previous embodiment, the second chamber 134a includes at least one openable seal, sealing the second chamber 134a. In the illustrated embodiment, the chamber 134a includes a bottom seal defined by head or stopper 120 of the plunger 118, wherein the head 120 covers and seals a bottom opening of the chamber 134a. Similar to that described above, the second chamber 134a has a gas pressure that changes from a first pressure to a second pressure, wherein the first pressure is less than the second pressure.

Referring to FIG. 7A, when the cartridge 102a is in the initial, unused and/or unopened state, the second chamber 134a is sealed and the first pressure of the gas pressure within the chamber 134a is such that the button 124a of the chamber 134a is held or maintained in a first position, shown in FIGS. 6 and 7A. In this first position, the biasing member 130a (spring) is placed into and held in a compressed state. In this arrangement, the first pressure of the gas pressure within the chamber 134a plus the force of the biasing member 130a (spring force) is less than the force of the external air pressure, and in one embodiment less than atmospheric pressure.

Referring to FIG. 9A, when the plunger 118 is advanced, the bottom seal is removed/broken and gas (e.g., air) enters the second chamber 134a through the bottom opening, increasing the gas pressure within the second chamber 134a to a second pressure, which is greater than the first gas pressure. When the gas pressure increases to the second pressure, the biasing member 130a pushes on the bottom of the button 124a, moving it upward within the second chamber 134a and away from the wall 132a of the cartridge 102a. In this second position, the force of the second pressure of the chamber 134a and the force of the biasing member 130a is greater than the outer surrounding air pressure. When the button is in the second position, it provides an indication that the cartridge 102a is opened and/or used.

Figure 10:
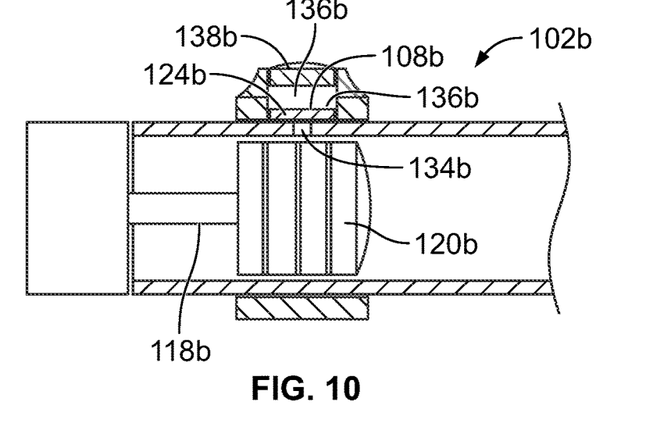
FIG. 10 is a cross-sectional view of the drug supply cartridge of FIG. 6, wherein the cartridge includes an alternative embodiment of a visual use indicator in accordance with the present disclosure.
Figure 11:
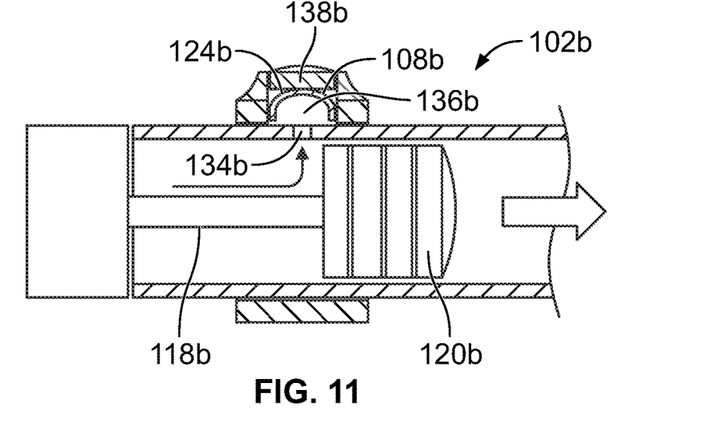
FIG. 11 is a cross-sectional view of the cartridge shown in FIGS. 6 and 10, wherein the visual use indicator has been moved into a position that indicates that the cartridge is in an opened and/or used state.

Turning to FIGS. 10 and 11, there is shown an alternative embodiment of a cartridge 102b. In this embodiment, the movable indicator 124b of the visual use indicator 108b includes a piece of elastic material (provided in the shape of a circle, for example). The piece 124b is naturally in a first configuration, such as in a cup-shaped configuration as shown in FIG. 11. The piece 124b may be placed into a second configuration under force, such as the straight configuration as shown in FIG. 10. Once the force is removed, the piece 124b returns back to the first configuration.

Referring to FIG. 10, the second or vacuum chamber 134b includes a top opening that is sealed by a top seal and a bottom opening that is sealed by a bottom seal. The piece 124b of elastic material is deformed into the second configuration where it covers the top opening of the second chamber 134b to seal the top opening. The bottom seal is defined by head 120b of the plunger 118b, wherein the head 120b covers and seals a bottom opening of the chamber 134b. The second chamber 134b has a gas pressure that changes from a first pressure to a second pressure, wherein the first pressure is less than the second pressure. When the cartridge 102b is in the initial, unused and/or unopened state, the second chamber 134b is sealed and the first pressure of the gas pressure within the chamber is such that the piece 124b is held in the deformed or second configuration. In this arrangement, the first pressure of the gas pressure within the chamber 134b plus the elastic force of piece 124b is less than the force of the external air pressure, and in one embodiment less than atmospheric pressure.

Referring to FIG. 11, when the plunger 118b is advanced, the bottom seal is removed/broken and gas enters the second chamber 134b through the bottom opening. The gas pressure within the second chamber 134b increases to a second pressure. When the gas pressure increases to the second pressure, the elastic force of the piece 124b moves the piece back into the first configuration, such as the illustrated U-shaped configuration. In the illustrated embodiment, the center of the piece 124b moves upward or away from the cartridge wall. Optionally, the piece may be within a third chamber 136b that includes a window or opening 138b. As shown in FIG. 10, in the unused and/or unopened state, piece 124b is not visible in the window or opening 138b of the third chamber. Referring to FIG. 11, in the opened and/or used state, when the pressure in the chamber changes, the portion of the piece 124b covering the opening is released and the middle section of the piece is moved into a position wherein it is visible to the user, thereby providing a visual indication that the cartridge 102b is opened and/or used.

Figure 12:
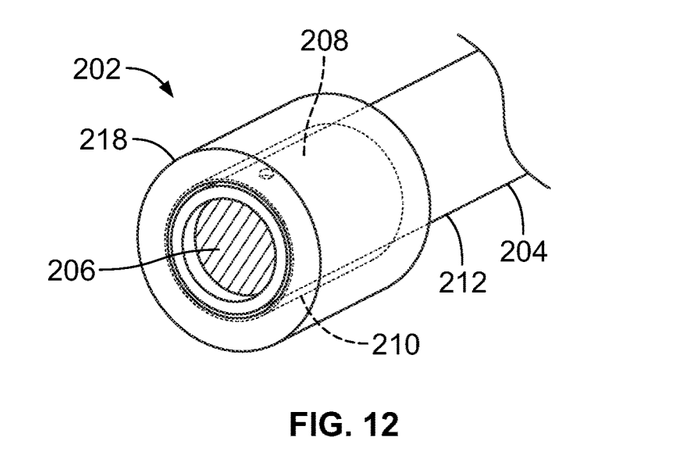
FIG. 12 is a top perspective view of another embodiment of a drug supply cartridge in accordance with the present disclosure, wherein a visual use indicator is in a position that indicates that the cartridge is in an unopened and/or unused state.
Figure 13:
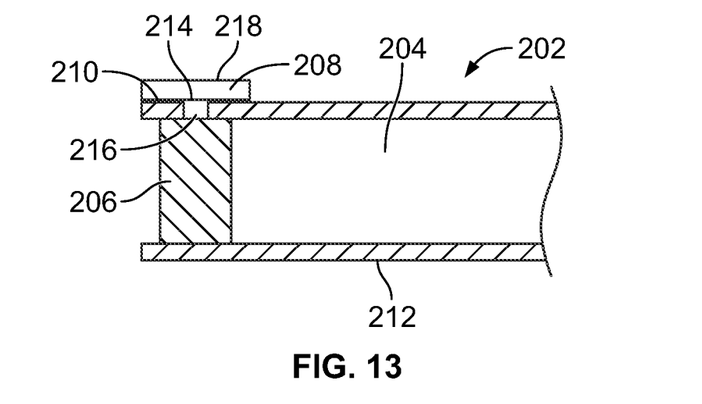
FIG. 13 is a cross-sectional view of the cartridge shown in FIG. 12.
Figure 14:
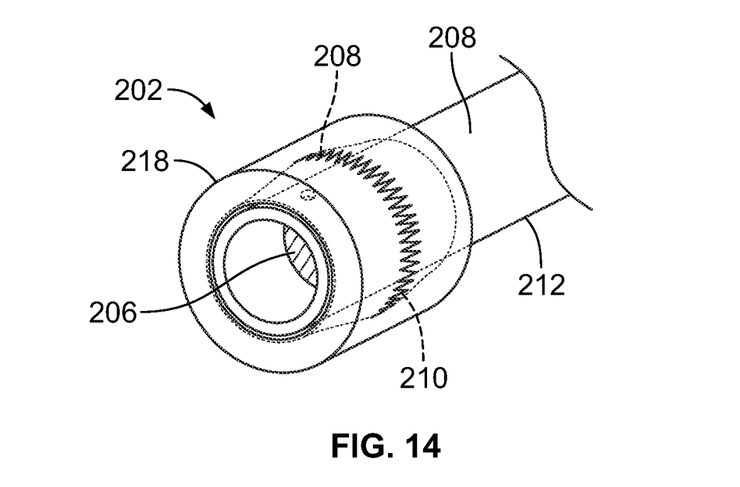
FIG. 14 is a perspective view of the cartridge shown in FIG. 12, wherein a plunger has been moved and the visual use indicator is moved into a position that indicates that the cartridge is in an opened and/or used state.
Figure 15:
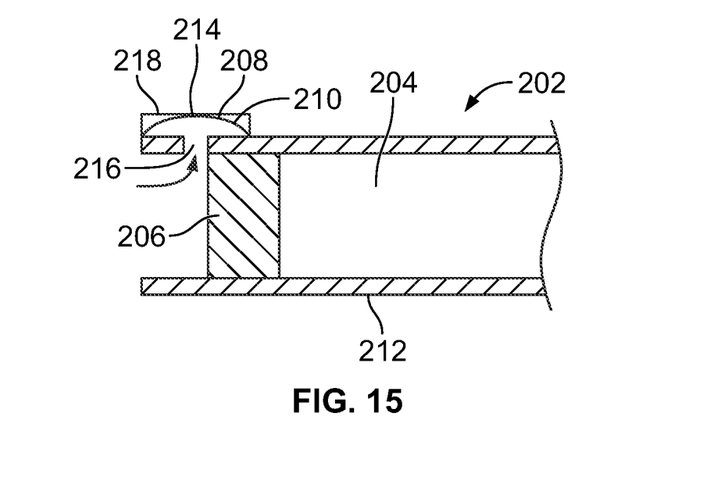
FIG. 15 is a cross-sectional view of the cartridge shown in FIG. 14.

Turning to FIGS. 12-15, there is shown an alternative embodiment of the cartridge 202. Similar to the previous embodiments, the cartridge 202 includes a first chamber 204 containing a drug and a plunger 206 for pushing/moving the drug to the delivery device. In this embodiment, the visual use indicator 208 includes a movable indicator, such as a band 210 of elastic material that is positioned around a barrel or body 212 of the cartridge 202. The elastic band 210 has a first, natural configuration, such as a curved configuration, wherein the band curves toward a peak 214 along the central line of the band. For example, the cross-section of the band 210 has the generally u-shaped shape, as shown in FIG. 15. The band 210 can be deformed into a second configuration. For example, the peak 214 along the central line may be flattened, so that the band 210 has a flat cross-sectional shape as shown in FIG. 13. The elastic band 210 may be placed into the second configuration under force, but once the force is removed, the band returns back to the first configuration.

Referring to FIGS. 12 and 13, the second or vacuum chamber 216 is defined by a hole through a wall of the cartridge 202. The second chamber 216 includes a top opening that is sealed by a top seal and a bottom opening that is sealed by a bottom seal. The elastic band 210 is deformed into the second configuration where it covers the top opening of the second chamber 216 to seal the top opening. The bottom seal is defined by plunger 206, wherein the plunger 206 covers and seals a bottom opening of the chamber 216. The second chamber 216 has a gas pressure that changes from a first pressure to a second pressure, wherein the first pressure is less than the second pressure. When the cartridge 202 is in the initial, unused and/or unopened state, the second chamber 216 is sealed and the first pressure of the gas pressure within the chamber is such that the band 210 is held in the deformed or second configuration. In this arrangement, the first pressure of the gas pressure within the chamber 216 plus the elastic force of band 210 is less than the force of the external air pressure, and in one embodiment less than atmospheric pressure.

Referring to FIGS. 14 and 15, when the plunger 206 is advanced, the bottom seal is removed/broken and gas enters the second chamber 216 through the bottom opening. The gas pressure within the second chamber 216 increases to a second pressure. When the gas pressure increases to the second pressure, the elastic force of the band 210 moves the band back into the first configuration, such as illustrated U-shaped configuration. In the illustrated embodiment, the center of the band 210 moves upward or away from the cartridge wall. Optionally, the band may be within a third chamber 218 that includes a window or opening or may be transparent or translucent. As shown in FIGS. 12 and 13, in the unused and/or unopened state, the band is not visible in the third chamber 218. Referring to FIGS. 14 and 15, in the opened and/or used state, when the pressure in the chamber changes, the portion of the band 210 covering the opening is released and the middle section of the band is moved into a position wherein it is visible to the user, thereby providing a visual indication that the cartridge 202 is opened and/or used.

Figure 16:
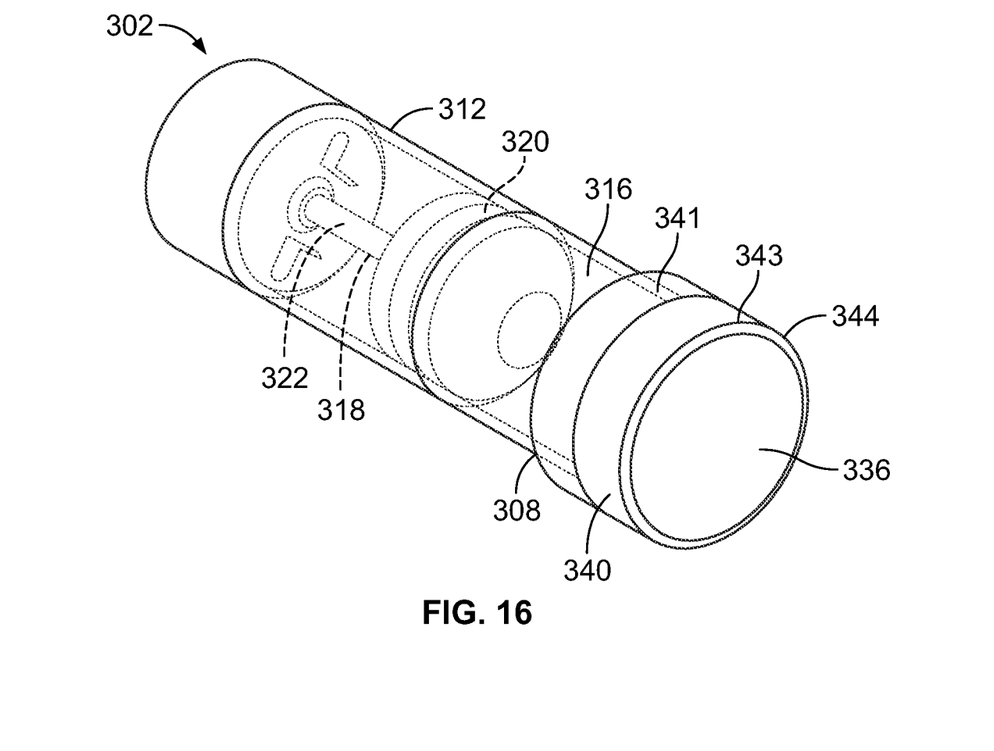
FIG. 16 is a perspective view of another embodiment of a drug supply cartridge in accordance with the present disclosure.
Figure 17:
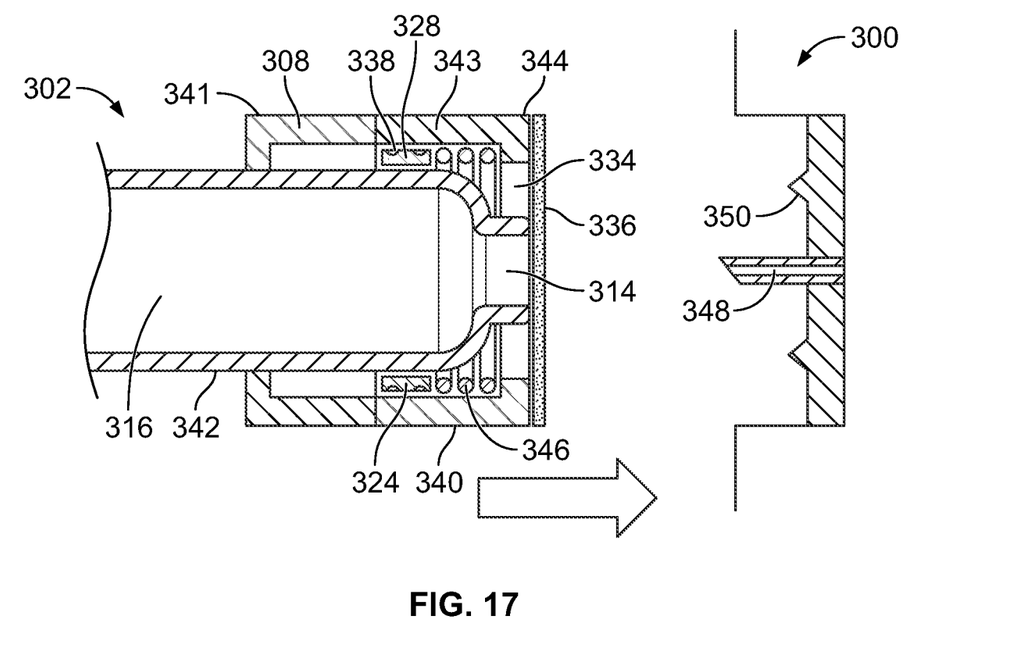
FIG. 17 is a cross-sectional schematic view showing the cartridge prior to being docked to a drug delivery device, wherein a visual use indicator of the cartridge is in a position that indicates that the cartridge is in an unopened and/or unused state.
Figure 18:
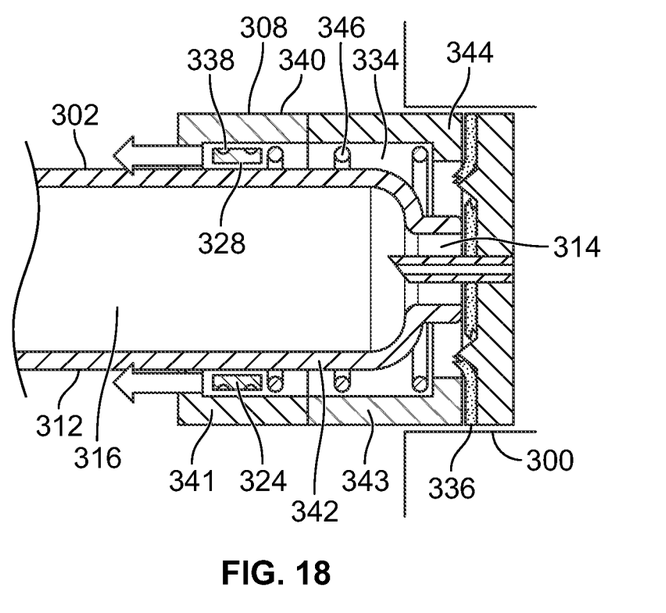
FIG. 18 is a cross-sectional schematic view of the cartridge and drug delivery device of FIG. 17, showing the cartridge being docked with the drug delivery device and the visual use indicator being moved into a position that indicates that the cartridge has been opened and/or used.

FIGS. 16-19 illustrate another alternative cartridge 302 that may be docked to a delivery device 300 (only a portion of which is shown in FIGS. 17 and 18). Cartridge 302 includes a body 312 having a shape and size suitable for docking with the delivery device 300. The cartridge 302 includes a port 314 (FIGS. 17 and 18) that fluidly connects to the delivery device 300 to supply the device with the drug to be injected. The cartridge 302 also includes a first chamber 316 that contains a drug or medicant. The first chamber 316 is in fluid communication with the port 314. A plunger 318 may be located in the first chamber 316. In the illustrated embodiment, the plunger 318 includes a head 320 and a rod 322. The plunger 318 is operatively connected to and controlled by the delivery device 300. The delivery device 300 moves the plunger 318 within the chamber 316 to push the drug out of the port 314 and into the delivery device 300.

Figure 19:
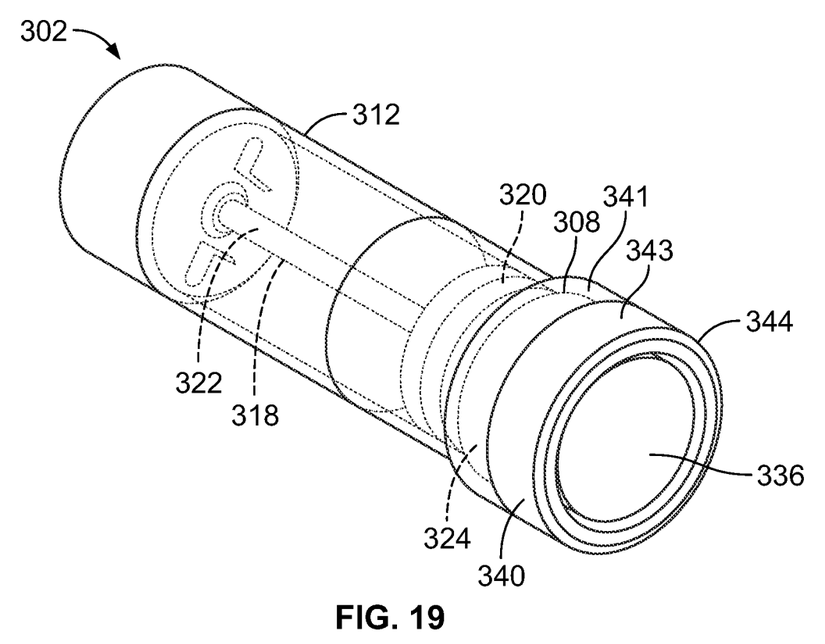
FIG. 19 is a perspective view of the drug supply cartridge of FIG. 16, wherein the visual use indicator is moved into a position that indicates that the cartridge has been opened and/or used.

The cartridge 302 includes a visual use indicator 308 that provides an indication of whether the cartridge 302 is unopened/unused or has been opened/used. FIGS. 16 and 17 illustrate the cartridge 302 in an unopened/unused state and prior to being docked in the delivery device 300. FIGS. 18 and 19 illustrate the cartridge 302 in the opened or used state. As can be seen by comparing these figures, in FIGS. 16 and 17, the visual indicator 308 includes a movable indicator 324 that is in a first position wherein the user cannot see the movable indicator. Absence of the indicator provides a visual indication that the cartridge 302 is in the unopened/unused stated. In FIGS. 18 and 19, the movable indicator 324 is moved to the second position where it can be seen by the user. Appearance of the movable indicator 324 provides a visual indication that the cartridge 302 is in the opened/used state.

Referring to FIGS. 17 and 18, in the illustrated embodiment, the movable indicator 324 is associated with a second chamber 334 that is movable from a collapsed configuration (FIG. 17) to an expanded configuration (FIG. 18). The second chamber 334 is at least partially defined by an outer wall or ring 340 that surrounds the proximal end 342 of the first chamber 316. As will be explained in more detail below, the outer wall has a transparent portion 341 and an opaque portion 343.

The second chamber 334 is further defined by an end seal 336 that is sealed to the proximal end 344 of the outer wall 340. This end seal 336 may be frangible, pierceable, breakable or otherwise removable. The end seal 336 may be made from, for example, a metal foil and/or a polymer layer. The end seal 336 may be sealed to the outer wall 340 in any suitable manner. Optionally, the seal 336 may cover the port 314 of the cartridge 302.

The movable indicator 324 defines the distal end of chamber 334 and is movable within the outer wall 340 and along the proximal end 342 of the first chamber 316. In the illustrated embodiment, the movable indicator 324 is a ring that is positioned around the first chamber 316/body 312 of the cartridge 302. The inner wall of the movable indicator 324 includes a circumferential inner wiper seal 328 that contacts the body 312 of the cartridge 302. The outer wall of movable indicator 324 also includes a circumferential outer wiper seal 338 that contacts the inner surface of the outer wall 340. The inner and outer wiper seals 328, 338 provide a gas-tight seal at the distal end of the second chamber 334. A biasing member 346 is located within the second chamber 334. The biasing member 346 may be, for example, any suitable biasing member, such as a helical spring. The biasing member 346 is located between the proximal end 344 of the outer wall 340 and the movable indicator 324. For example, the biasing member 346 may be between a shoulder or lip of the outer wall 340 and a proximal end or surface of the movable indicator 324. The biasing member 346 biases the movable indicator 324 distally and away from the proximal end 344 of outer wall 340. Thus, the biasing member 346 biases the second chamber 334 toward the expanded state as shown in FIG. 18. In the expanded state, the indicator is moved into a position aligned with the transparent portion 341 of the outer wall 340 to indicate that the cartridge 302 has been opened and/or used.

Referring to FIGS. 16 and 17, in the unopened and/or unused state, the second chamber 334 includes a vacuum, wherein the first gas pressure inside of the chamber 334 is less than the gas pressure outside of the chamber 334. In this unopened and/or unused state, the first pressure of the gas pressure within the chamber 334 plus the force of the biasing member 346 is less than the force of the external air pressure. In one embodiment the first gas pressure is less than atmospheric pressure. In this arrangement, the second chamber 334 is held in the compressed state wherein the movable indicator 324 is in a position that is aligned with the opaque portion 343 of the outer wall 340 and held away from the transparent portion 341 of the outer wall 340. Thus, the movable indicator 324 is not visible to the user.

Referring to FIGS. 17-19, when the cartridge 302 is docked to the delivery device 300, the proximal end seal 336 is punctured or broken. In the illustrated embodiment, the delivery member 300 includes a needle 348 and one or more piercing members 350. When the cartridge 302 is docked to the delivery device 300, the needle 348 pierces the end seal 336 and enters the port, and the one or more piercing members 350 also pierce the seal 336. This piercing of the seal 336 allows gas to enter the chamber 334 such that the gas pressure within the chamber 334 increases to a second gas pressure. In this position, the force of the second pressure of the chamber 334 and the force of the biasing member 346 is greater than the outer surrounding air pressure. This allows the biasing member 346 to push the movable indicator 324, expanding the chamber 334. The movable indicator 324 moves within the outer wall 340 and in line with the transparent portion 341 of the outer wall. The movable indicator 324 is now visible to the user, indicating that the cartridge 302 has been opened and/or used.

It will be understood that the embodiments and examples described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

The invention claimed is:

1. A replaceable cartridge containing a liquid drug, comprising:
  a first chamber containing a liquid drug;
  a second chamber including an openable seal, the second chamber having a gas pressure, wherein the gas pressure of the second chamber changes from a first pressure to a second pressure when the openable seal is opened;
  a movable visual indicator associated with the second chamber, the movable visual indicator being in a first position when the gas pressure of the second chamber is the first pressure, and the movable visual indicator moving to a second position when the gas pressure of the second chamber is the second pressure, thereby indicating that the replaceable cartridge is in an opened and/or used state; and
  a biasing member that biases the movable visual indicator toward the second position, wherein the biasing member exerts a force on the movable visual indicator while the movable visual indicator is in the first position and the gas pressure of the second chamber is the first pressure.

2. The replaceable cartridge of claim 1, wherein the movable visual indicator is not visible in the first position.

3. The replaceable cartridge of claim 2, wherein the movable visual indicator is visible in the second position.

4. The replaceable cartridge of claim 1, wherein the biasing member comprises a spring.

5. The replaceable cartridge of claim 1, wherein the biasing member exerts a continuous force on the movable visual indicator.

6. The replaceable cartridge of claim 1, wherein the biasing member is positioned between the movable visual indicator and a wall.

7. The replaceable cartridge of claim 6, wherein the biasing member is held in a compressed state between the movable visual indicator and the wall while the visual indicator is in the first position.

8. The replaceable cartridge of claim 1, further including a plunger, wherein the openable seal is defined by the plunger.

9. The replaceable cartridge of claim 1, wherein the openable seal comprises a pierceable seal.

10. The replaceable cartridge of claim 1, wherein the first pressure is a vacuum pressure.

11. A drug delivery device, comprising:
  a housing containing a drug delivery mechanism; and
  a replaceable cartridge containing a liquid drug, wherein the replaceable cartridge is configured to be inserted into the housing and in communication with the drug delivery mechanism, the replaceable cartridge comprising:
    a first chamber containing the liquid drug;
    a second chamber including an openable seal, the second chamber having a gas pressure, wherein the gas pressure of the second chamber changes from a first pressure to a second pressure when the openable seal is opened;
    a movable visual indicator associated with the second chamber, the movable visual indicator being in a first position when the gas pressure of the second chamber is the first pressure, and the movable visual indicator moving to a second position when the gas pressure of the second chamber is the second pressure, thereby indicating that the replaceable cartridge is in an opened and/or used state; and
    a biasing member that biases the movable visual indicator toward the second position, wherein the biasing member exerts a force on the movable visual indicator while the movable visual indicator is in the first position and the gas pressure of the second chamber is the first pressure.

12. The drug delivery device of claim 11, wherein the movable visual indicator is not visible in the first position.

13. The drug delivery device of claim 12, where in the movable visual indicator is visible in the second position.

14. The drug delivery device of claim 11, wherein the biasing member comprises a spring.

15. The drug delivery device of claim 1, wherein the biasing member exerts a continuous force on the movable visual indicator.

16. The drug delivery device of claim 11, the biasing member is positioned between the movable visual indicator and a wall.

17. The drug delivery device of claim 16, wherein the biasing member is held in a compressed state between the movable visual indicator and the wall while the visual indicator is in the first position.

18. The drug delivery device of claim 11, further including a plunger, wherein the openable seal is defined by the plunger.

19. The drug delivery device of claim 11, wherein the openable seal comprises a pierceable seal.

20. The drug delivery device of claim 11, wherein the first pressure is a vacuum pressure.

* * * * *